(12) United States Patent
Dubois

(10) Patent No.: US 8,686,195 B2
(45) Date of Patent: Apr. 1, 2014

(54) METHOD FOR SYNTHESIZING ACROLEIN FROM GLYCEROL

(75) Inventor: Jean Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/518,021

(22) PCT Filed: Dec. 7, 2010

(86) PCT No.: PCT/FR2010/052626
§ 371 (c)(1),
(2), (4) Date: Jul. 23, 2012

(87) PCT Pub. No.: WO2011/083225
PCT Pub. Date: Jul. 14, 2011

(65) Prior Publication Data
US 2012/0283479 A1    Nov. 8, 2012

(30) Foreign Application Priority Data
Dec. 22, 2009   (FR) ...................................... 09 59379

(51) Int. Cl.
*C07C 45/75* (2006.01)
(52) U.S. Cl.
USPC ....................................................... 568/461
(58) Field of Classification Search
USPC ....................................................... 568/461
See application file for complete search history.

(56) References Cited

U.S. PATENT DOCUMENTS

| | | |
|---|---|---|
| 4,222,965 A | 9/1980 | Gorbunov et al. |
| 7,396,962 B1 * | 7/2008 | Dubois et al. ................. 568/485 |

FOREIGN PATENT DOCUMENTS

FR   2 230 613  A1   12/1974

OTHER PUBLICATIONS

International Search Report of PCT/FR2010/052626 (Feb. 16, 2011).
A. Corma et al., "Biomass to Chemicals: Catalytic Conversion of Glycerol/Water Mixtures into Acrolein, Reaction Network", Journal of Catalysis, vol. 257, No. 1 (2008) pp. 163-171.

* cited by examiner

*Primary Examiner* — Sikarl Witherspoon
(74) *Attorney, Agent, or Firm* — Millen, White, Zelano & Branigan, P.C.

(57) ABSTRACT

The present invention relates to a process for synthesizing acrolein, coupling the dehydration of glycerol into acrolein with a reaction for aldol condensation of acetaldehyde, produced in the form of an impurity during the dehydration, by means of formaldehyde.

More particularly, the process according to the invention consists in subjecting the gaseous effluent resulting from the glycerol dehydration reaction to cooling, then in first of all carrying out, in a first zone, washing with water and condensation of said gaseous effluent so as to then separate, in a second fractionation zone, firstly, a stream rich in light aldehydes, secondly, a stream rich in water and, thirdly, the acrolein stream, and then in reacting the acetaldehyde contained in the light aldehydes-rich stream resulting from the preceding step with formaldehyde so as to obtain a second acrolein-rich stream by means of an aldol condensation reaction according to the following reaction scheme: $CH_3-CHO+CH_2O \rightarrow CH_2=CH-CHO+H_2O$ and in recycling this second acrolein-rich stream to the preceding step.

14 Claims, 6 Drawing Sheets

METHOD FOR SYNTHESIZING ACROLEIN FROM GLYCEROL

The present invention relates to a process for synthesizing acrolein, coupling the dehydration of glycerol into acrolein with a reaction for aldol condensation of acetaldehyde, produced in the form of an impurity during the dehydration, by means of formaldehyde.

Acrolein is the usual name given to the unsaturated aldehyde of formula $CH_2=CH-CHO$ called propenal. This compound has been known for a very long time and is used as a broad-spectrum biocide; it is also an intermediate for the synthesis of various products such as D,L-methionine (supplement for animal feed), acrylic acid, pharmaceutical products, fungicides, fragrances, pyridine, picolines, glutaraldehyde, etc.

The major industrial processes for producing acrolein are today the one developed by the company Degussa during the 1940s using acetaldehyde and formol as raw materials, and the one set up some 20 years later by various companies, consisting in oxidizing propylene. The Degussa process carried out in the gas phase by heterogeneous catalysis is based on the following reaction:

$$CH_3-CHO+CH_2O \rightarrow CH_2=CH-CHO+H_2O.$$

The second process, which from an industrial point of view has supplanted the previous one, is based on the following oxidation reaction:

$$CH_2=CH-CH_3+O_2 \rightarrow CH_2=CH-CHO+H_2O.$$

More recently, considerable work has been carried out in order to upgrade another process for synthesis from glycerol subjected to dehydration according to the following reaction:

$$CH_2OH-CHOH-CH_2OH \rightarrow CH_2=CH-CHO+2H_2O.$$

This type of process has the huge advantage of being able to work with a non-fossil natural raw material and therefore of satisfying, by producing what is referred to as a bio-based acrolein, the commitments of most industrialized countries aiming to reduce greenhouse gas emissions with the environmental effects thereof.

The term "bio-based" acrolein is intended to mean a compound which has a $^{14}C$ carbon content characteristic of the non-fossil natural origin of the raw materials used.

The use of carbon-based raw materials of natural and renewable origin can be detected by means of the carbon atoms which go to make up the composition of the final product. Indeed, unlike matter derived from fossil materials, matter composed of renewable raw materials contains $^{14}C$. All carbon samples taken from living (animal or plant) organisms are in fact a mixture of 3 isotopes: $^{12}C$ (representing ~98.892%), $^{13}C$ (~1.108%) and $^{14}C$ (traces: $1.2 \times 10^{10}$%). The $^{14}C/^{12}C$ ratio of living tissues is identical to that of the atmosphere. In the environment, $^{14}C$ exists in two predominant forms: in inorganic form, i.e. carbon dioxide ($CO_2$), and in organic form, i.e. carbon integrated into organic molecules.

In a living organism, the $^{14}C/^{12}C$ ratio is kept constant by the metabolism since carbon is continually exchanged with the environment. Since the proportion of $^{14}C$ is substantially constant in the atmosphere, the same is true in the organism, as long as it is alive, since it absorbs this $^{14}C$ like it absorbs $^{12}C$. The average $^{14}C/^{12}C$ ratio is equal to $1.2 \times 10^{-12}$.

$^{12}C$ is stable, i.e. the number of $^{12}C$ atoms in a given sample is constant over time. $^{14}C$, itself, is radioactive and each gram of carbon of a living being contains sufficient $^{14}C$ isotope to give 13.6 disintegrations per minute.

The half-life (or period) $T_{1/2}$, linked to the disintegration constant, of $^{14}C$ is 5730 years. Given this amount of time, it is considered that the $^{14}C$ content is virtually constant from the extraction of the plant raw materials to the production of the final product.

At the current time, there are at least two different techniques for measuring the $^{14}C$ content of a sample:
- by liquid scintillation spectrometry,
- by mass spectrometry: the sample is reduced to graphite or to $CO_2$ gas, and analyzed in a mass spectrometer. This technique uses an accelerator and a mass spectrometer for separating the $^{14}C$ ions from the $^{12}C$ ions, and therefore determining the ratio of the two isotopes.

These methods for measuring the $^{14}C$ content of materials are precisely described in standards ASTM D 6866 (in particular D 6866-06) and in standards ASTM D 7026 (in particular 7026-04). The method of measurement preferentially used is the mass spectrometry described in standard ASTM D6866-06 ("accelerator mass spectroscopy").

The subject of the invention is a process for synthesizing "bio-based" acrolein having a $^{14}C$ content by weight such that the $^{14}C/^{12}C$ ratio is between $0.2 \times 10^{-12}$ and $1.2 \times 10^{-12}$. Preferably, the $^{14}C/^{12}C$ ratio is between $0.6 \times 10^{-12}$ and $1.2 \times 10^{-12}$, and more preferably between $0.9 \times 10^{-12}$ and $1.2 \times 10^{-12}$.

The $^{14}C/^{12}C$ ratio will depend on the methods of production implemented, and on the raw materials used, entirely or partially of non-fossil natural origin, or according to mixtures subsequently made. This ratio cannot exceed $1.2 \times 10^{-12}$; if it does, this would imply that the operator has artificially introduced $^{14}C$ atoms into the acrolein compound.

The known processes for producing bio-based acrolein from glycerol result, however, in yields that remain overall insufficient. These low yields are explained partly by the presence in the effluent leaving the reactor of large amounts of by-products such as acetaldehyde and formaldehyde, resulting from decomposition of the glycerol, the acrolein or other intermediates. A substantial part of the raw material, about from 5 to 10%, can thus be lost in the form of by-products. In the article J. Catal., 257, 163-171 (2008), A. Corma et al. suggest separating and isolating the acetaldehyde in order to commercially exploit it.

The objective of the invention is to overcome the above drawbacks by proposing a process for synthesizing "bio-based" acrolein using mainly non-fossil natural raw materials and offering a greater yield.

The subject of the present invention is therefore a process for synthesizing acrolein from glycerol, offering the best possible acrolein yield, but also the best way to exploit the by-products, generally lost in the amount of from 5 to 10% of the raw material, in particular the best possible exploitation of the acetaldehyde contained in the acrolein stream resulting from the glycerol dehydration reaction.

The process for synthesizing acrolein according to the invention consists
- in a first step, in subjecting a glycerol charge resulting from the methanolysis of plant oils or of animal fats to a dehydration reaction resulting in acrolein according to the reaction $CH_2OH-CHOH-CH_2OH \rightarrow CH_2=CH-CHO+2H_2O$, then,
- in a second step, after having subjected the effluent resulting from the first step to cooling, in carrying out first of all, in a first zone, washing with water and condensation of the gaseous effluent resulting from the first step, so as to then separate, in a second fractionation zone, firstly a light aldehydes-rich stream, secondly a water-rich stream and thirdly the acrolein stream, then, in a third step, in reacting the acetaldehyde contained in the light aldehydes-rich stream resulting from the preceding step with formaldehyde so as to obtain an acrolein-rich second stream by aldol condensation reaction according to the following reaction scheme: $CH_3$—CHO+ $CH_2O \rightarrow CH_2$=CH—CHO+$H_2O$ and in recycling this acrolein-rich second stream to the preceding step 2.

Although the aldol condensation reaction between the acetaldehyde and the formaldehyde so as to produce acrolein is known from the prior art, no document suggests the advantages of the present invention linked to the combination of this reaction with a process for synthesizing acrolein from glycerol.

The charge used in the 1st step of the first process is glycerol—1,2,3-propanetriol—which is a co-product formed during methanolysis, or more generally alcoholyses, hydrolyses and saponification, of plant oils or of animal fats, the other co-product being the methyl esters which are used in particular as diesel oil and domestic fuel, or fatty acids (hydrolysis) or soaps (saponification). The development of "biofuels" leads to an increase in the production of glycerol according to this route, where glycerol represents about 10% of the weight of the oil converted.

The glycerol may be subjected beforehand to various purification treatments aimed at removing the salts by distillation, by using ion exchange resins or by using a fluidized bed (French patent application 2 913 974), or purification and evaporation of the glycerol, in particular described by G. B. D'Souza, in J. Am. Oil Chemists' Soc. November 1979 (Vol 56) 812A, by Steinberner U et al., in Fat. Sci. Technol. (1987), 89 Jahrgang No. 8, pp. 297-303, and by Anderson D. D. et al. in Soaps and Detergents: A theoretical and Practical Review, Miami Beach Fla., Oct. 12-14, 1994, chapter 6 pp. 172-206. Ed: L Spitz, AOCS Press, Champaign.

Aqueous solutions of glycerol of which the concentration can vary to large extents, for example 20 to 99% by weight of glycerol, are generally used, solutions comprising from 30 to 80% by weight of glycerol are preferably used.

The dehydration reaction

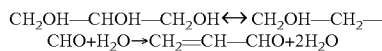
$CH_2OH$—CHOH—$CH_2OH \leftrightarrow CH_2OH$—$CH_2$—
CHO+$H_2O \rightarrow CH_2$=CH—CHO+$2H_2O$ is an equilibrated reaction which is favored by a high temperature level. It is generally carried out in the gas phase in the reactor in the presence of a solid catalyst at a temperature ranging from 150° C. to 500° C., preferably between 250° C. and 350° C., and a pressure between 1 and 5 bar. It can also be carried out in the liquid phase, as is described in U.S. Pat. No. 5,387,720, column 3, line 13, to column 4, line 11. It can also be carried out in the presence of oxygen or of an oxygen-containing gas as described in applications WO 06/087083 and WO 06/114506. In these processes, the oxygen does not have an oxidation function, but in fact contributes to decoking the catalyst, by burning off the coke formed. This catalyst is not an oxidizing catalyst, in the sense that it forms little acrylic acid and acetic acid, but is an acid catalyst, and it rapidly becomes fouled up and decoking it therefore makes it possible to prolong its lifetime; in addition, the oxygen also contributes to reducing the formation of bothersome by-products such as phenol, acetone and propanaldehyde, for example. As long as the temperature is not too high, there is no oxidation to acrylic acid.

The glycerol dehydration reaction is generally carried out on acidic solid catalysts. The catalysts that are suitable are homogeneous or multiphase materials, which are insoluble in the reaction medium and which have a Hammett acidity, denoted $H_0$, of less than +2.

As indicated in U.S. Pat. No. 5,387,720, which makes reference to the article by K. Tanabe et al., in "Studies in Surface Science and Catalysis", vol. 51, 1989, chap. 1 and 2, the Hammett acidity is determined by amine titration using indicators or by adsorption of a base in the gas phase.

These catalysts can be chosen from natural or synthetic silicious materials or acidic zeolites; mineral supports, such as oxides, coated with mono-, di-, tri- or polyacidic inorganic acids; oxides or mixed oxides, or alternatively heteropolyacids or heteropolyacid salts.

These catalysts may generally consist of a heteropolyacid salt in which protons of said heteropolyacid are exchanged with at least one cation chosen from the elements belonging to Groups I to XVI of the Periodic Table of Elements, these heteropolyacid salts containing at least one element chosen from the group comprising W, Mo and V.

Among the mixed oxides, mention may in particular be made of those based on iron and on phosphorus, those based on vanadium and phosphorus, those based on aluminum and phosphorus, boron and phosphorus, phosphorus or silicon and tungsten and those based on cesium, phosphorus and tungsten.

The catalysts are in particular chosen from zeolites, Nafion® composites (based on fluoropolymer sulfonic acid), chlorinated aluminas, phosphotungstic and/or silicotungstic acids and acid salts, and various solids of metal oxide type, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2$—$Al_2O_3$, impregnated with acid functions such as borate $BO_3$, sulfate $SO_4$, tungstate $WO_3$, phosphate $PO_4$, silicate $SiO_2$ or molybdate $MoO_3$ or a mixture of these compounds.

The previous catalysts may in addition comprise a promoter such as Au, Ag, Cu, Pt, Rh, Pd, Ru, Sm, Ce, Yt, Sc, La, Zn, Mg, Fe, Co or Ni.

The preferred catalysts are phosphate zirconias, tungsten zirconias, silicious zirconias, titanium or tin oxides impregnated with tungstate, silicotungstate or phosphotungstate, phosphate aluminas or silicas, heteropolyacids or heteropolyacid salts, iron phosphates and iron phosphates comprising a promoter, and vanadium-phosphorus mixed oxides.

In the event of the reaction being carried out in the liquid phase, the catalysts used, of the same nature as the previous ones, shall themselves have a Hammett acidity $H_0$ of generally less than +2, preferably of between −20 and −8.2. This form of implementation of the reaction described in the publication by Benjamin Katryniok et al. "Towards the Sustainable Production of Acrolein by Glycerol Dehydration" published in ChemSusChem 2009, 2,719-730 Ed. Wiley, poses problems, however, from an industrial point of view owing to the very high pressure conditions and, furthermore, the selectivity of the reaction as soon as it is sought to increase the conversion rate. This is the reason why the liquid-phase process has not so far been adopted by manufacturers; it should, however, be noted that the process of the invention makes it possible to solve the problem posed by the selectivity and therefore to substantially improve the performance levels of a liquid-phase process.

The second step is carried out in an assembly consisting of a condensation, generally called absorption/desorption, zone comprising at least two columns, the first making it possible to remove the heavy compounds and the second enabling desorption of the noncondensable compounds. The term "column" should be understood to mean column but also heat exchanger, condenser or any equivalent system. The assembly also comprises a fractionation zone comprising at least one distillation column enabling separation, firstly, of the aqueous fraction of the solution and, secondly, of the acrolein-rich stream and of the lighter stream enriched in light aldehydes such as, for example, acetaldehyde.

The gaseous effluent derived from the dehydration reactor is subjected, on leaving said reactor, to quench cooling in any suitable device such as a "gas-fired boiler—heat exchanger" allowing the production of vapor, and then conveyed into the condensation zone where it is washed with water, allowing absorption of most of the constituents of the gaseous effluent, in an absorption/condensation column, operating at a temperature of generally between 0 and 90° C., the temperature of the gases at the top of the column preferably being between 30 and 60° C. and that of the liquid at the bottom of the column between 60 and 90° C. In this column, the acrylic acid, the acetic acid, but also the glycerol polyethers, the glycerol acetals, the residual glycerol, etc., are separated at the bottom, while the acrolein, the acetaldehyde, the formaldehyde, the acetone, the propionaldehyde and the gases which have not reacted, $O_2$, $N_2$, etc., and also CO, $CO_2$, etc., are given off at the top of the column. The effluent at the top of this first column is conveyed to a second column for removing the noncondensable compounds (light gases), at the bottom of which an aqueous solution of acrolein containing the light compounds that are soluble under the conditions is collected, the noncondensable compounds being flushed off at the top of the column. The aqueous solution of acrolein is sent to the zone for fractionation by distillation in order to separate a fraction of light aldehydes containing the acetaldehyde and also other light compounds such as the formaldehyde and a heavier fraction containing the acrolein and often also propanaldehyde and acetone in solution in water, said heavier fraction including the aqueous solvent which, extracted after separation by distillation, can be recycled.

In one variation of implementation of the condensation zone, the absorption column will be coupled with another column to which the effluent from the bottom of the absorption/condensation column will be sent in order to allow better separation of the heavy compounds and recovery of the lighter compounds having been entrained in this heavy fraction.

As regards the fractionation zone, it will generally comprise at least two successive distillation columns; at the top of the first column, the stream rich in light aldehydes, acetaldehyde and other light compounds will be extracted and the liquid effluent from the bottom of this first column will be transferred into a second column in which the acrolein stream will be separated at the top and the aqueous effluent at the bottom.

In one variation of implementation of this fractionation zone, the acrolein, the light aldehydes and the water will be separated in a single column with a side-draw take-off as described in U.S. Pat. No. 6,515,187. "Compacted" columns of this type make it possible to limit capital investment. They are also illustrated by the schemes which appear in the Techniques de l'Ingénieur J6100, page 2, and in Ullmann's and Kirk Othmer's encyclopedias, pages 154 and 287, for example.

The light fraction recovered at the top of the distillation column, rich in light aldehydes such as acetaldehyde and formaldehyde, is sent to the third step, optionally after additional purification treatments.

The composition of this light aldehydes-rich light fraction depends on the operating conditions of the dehydration reaction and also on those of the absorption/desorption phases. Generally, the acetaldehyde content is substantially higher than the formaldehyde content. However, this does not mean that the acetaldehyde content will be systematically greater than the formaldehyde content in this light aldehydes-rich light fraction. In summary, this light fraction will always contain acetaldehyde and a variable amount of formaldehyde depending on the operating conditions.

During the third step, the acetaldehyde resulting from the preceding step is reacted with formaldehyde according to an aldol condensation reaction of which the reaction scheme is described below. The acetaldehyde will be introduced into the aldol condensation reactor via the stream constituting the light aldehydes-rich light fraction resulting from step 2, which is rich in acetaldehyde. The formaldehyde will be introduced into the aldol condensation reactor, firstly, via the stream constituting the light aldehydes-rich light fraction and, secondly, in the form of fresh formaldehyde. Should the formaldehyde content of the light aldehydes-rich light fraction be such that the formaldehyde/acetaldehyde ratio is greater than that set for carrying out the reaction, fresh acetaldehyde will be introduced into the aldol condensation reaction in order to achieve said ratio. An additional acrolein stream is thus obtained via an aldol condensation reaction. This additional stream is then recycled to step 2. This reaction is carried out in the gas phase at a temperature of between 150 and 400° C., preferably between 260 and 350° C., at an hourly space velocity (VVH) of from 100 to 2500 $h^{-1}$, at a pressure generally between 0.5 and 10 bar, preferably between 0.8 and 2 bar, in the presence of a solid condensation catalyst. A polymerization inhibitor, such as phenothiazine, hydroquinone, hydroquinone monomethyl ether, di-tert-butylpara-cresol (BHT), para-phenylenediamine or a Tempo derivative, can be added to the aldol condensation reactor.

The solid condensation catalysts that can be used in the process of the invention are generally natural or synthetic oxides (zeolites, for example), of which the range is very broad, but which must have certain characteristics. Indeed, the condensation (aldol condensation) reaction is in fact a two-step reaction during which a hydroxylated aldehyde is first of all formed, which then results in the unsaturated aldehyde via dehydration. The performing of these two steps requires a catalyst which has acidic sites but which must also preferably have basic sites in order to carry all the reactions through to a successful conclusion.

The best catalysts will be selected on the basis of two criteria linked to the adsorption of test molecules: $NH_3$ (acidity), $CO_2$ and $SO_2$ (basicity).

The first criterion is the average heat of adsorption of these test molecules on said solid. The method for measurement by differential scanning microcalorimetry is described in the Handbook of Thermal Analysis and calorimetry; vol. 5, Chapter 11, pages 387-438 "Heterogeneous Catalysis on Solids".

The average $CO_2$ adsorption heat will have to be between 40 kJ/mol and 170 kJ/mol at 303° K.

The average $SO_2$ adsorption heat will have to be between 25 kJ/mol and 180 kJ/mol at 353° K.

The average $NH_3$ adsorption heat will have to be between 25 kJ/mol and 170 kJ/mol at 423° K.

The second criterion is the amount of these test molecules adsorbed per unit surface area of these solids as described in the article "Microcalorimetric Study of the Acidity and Basicity of Metal Oxide Surfaces" by Mine Auroux and Antonella Gervasini published in J. Phys. Chem. 1990, 94, 6371-6379.

The amount of $NH_3$ adsorbed on the surface of the catalyst will be between 1.5 and 8 micromol/$m^2$ and that of $CO_2$ between 0.5 and 8 micromol/$m^2$.

By way of examples of constituents of the solid catalyst, mention may be made of: BaO, SrO, CaO, MgO, ZnO, $TiO_2$, $ZrO_2$ in oxide or carbonate form, clay-type oxides such as hydrotalcites, chrysotile and sepiolite, zeolites exchanged with alkali metal (Cs, K, Na, Li) ions, alkali metal fluorides (such as KF, for example) deposited on alumina, rare earth oxides or oxycarbonates, solids of the type such as alkali metals supported on alumina (such as Na/Al$_2$O$_3$) or on magnesia (such as Li/MgO), or rare earth oxides doped with alkaline-earth metals, such as (SrO—La$_2$O$_3$).

This solid catalyst will for example consist of sodium silicate on silica, or of a silica-alumina preferably having an Si/Al atomic ratio of greater than 10, comprising, where appropriate, a promoter. By way of example of such catalysts, mention may also be made of crystalline or amorphous aluminosilicates, silicalites, crystalline synthetic zeolites such as faujasite, ferrierite, ZSM-5, in their acid form or either partially or totally neutralized with elements of groups 1 to 14, and preferably groups 1 and 2, and with Zn and Tl. The zeolites used can have, in their structure, some or all of the aluminum atoms replaced with trivalent atoms such as B, Ga, Fe, Cr, V, As, Sb, Bi or Be, and can have some or all of the silicon atoms replaced with tetravalent atoms such as Ge, Ti, Zr or Hf.

Other catalysts may also be suitable for this reaction, for instance mixed oxide catalysts such as mixed phosphates of cobalt and aluminum, alumina, silica or silica-alumina doped for example with sodium (Na), potassium (K), cesium (Cs), cadmium (Cd), Mg, Ca, Sr, Mn, Zn, Mo, Nb, Pb or Si salts. They may be MgO-alumina, MgO—SiO$_2$, etc., rare earths, in the form of phosphates, tungstates, molybdates, etc. Hydrotalcites, hydroxyapatites, oxynitrides of phosphorus-containing derivatives, such as mixed oxynitrides of vanadium-aluminum, phosphorus-zirconium, phosphorus-aluminum, vanadium-aluminum-phosphorus or gallium-aluminum-phosphorus, may also be suitable for this reaction. Likewise, use may be made of the basic solids as defined in table 1.2 Solid Bases of the publication "Definition and Classification of Solid Acids and Bases, Their Catalytic Properties", of the handbook "New Solid Acids and Bases" by Tanabe et al., Kodansha, Tokyo, 1989, pages 1 to 3, and pages 326 to 329.

The most important factor for directing the selectivity toward one molecule or other lies in the nature and the respective amounts of the reactants involved. Formaldehyde is added to the reaction medium in an amount such that the formaldehyde/acetaldehyde mole ratio is between 0.3 and 1.5, preferably between 0.5 and 1.0.

The reaction is preferably carried out in the presence of oxygen or air, which will make it possible to avoid rapid deactivation of the catalyst. The catalyst can, however, be regenerated by air treatment at a temperature of between 250 and 550° C.

Reaction scheme

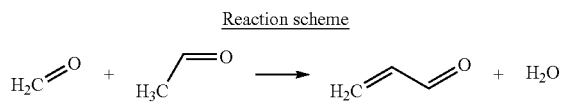

Under the synthesis conditions, other reactions can exceptionally take place depending on the molecules (impurities) present in the medium, such as, for example:

Production of Crotonaldehyde (2-butenal)

Production of Methacrolein and Pentenal

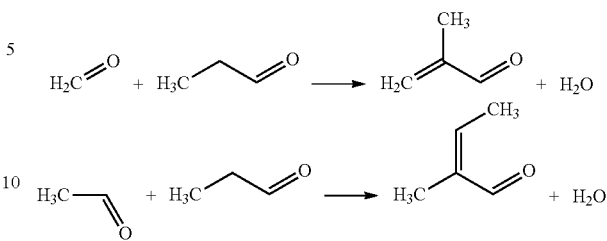

However, it is possible to avoid the formation of this pentenal compound, obtained by cross aldol condensation of acetaldehyde and of propanaldehyde, and this methacrolein compound by making sure that propanaldehyde is not present with acetaldehyde in the light aldehydes fraction.

On the other hand, the production of pentaerythritol must be considered in the process scheme. In order to limit the formation of this heavy product, the formaldehyde/acetaldehyde ratio must preferably be kept below 1. Preferably, the reaction will therefore be carried out with total conversion of the formaldehyde and partial conversion of the acetaldehyde.

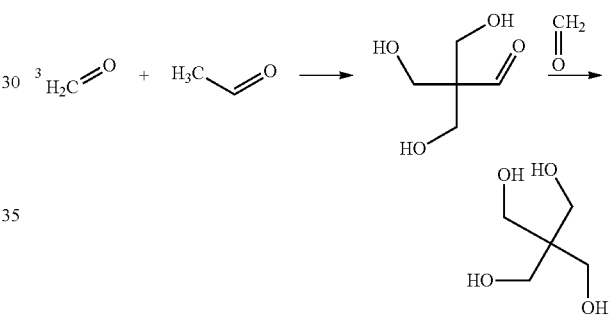

The composition of the mixture entering the reactor for synthesis of acrolein by aldol condensation determines in part the mole ratios in which the various products synthesized—acrolein and crotonaldehyde (2-butenaldehyde)—are obtained.

On leaving the aldol condensation reactor, the gaseous effluent containing the acrolein is cooled and recycled to the condensation step 2. This stream can be introduced as additional charge at the input of the condensation zone in step 2, where it undergoes all the treatments of the main chain of purification of the acrolein produced by dehydration of glycerol. It can also be introduced at an intermediate point of the condensation zone of step 2, after removal of the noncondensable compounds Finally, it can be introduced at the input of the fractionation zone of step 2.

This embodiment of the process of the invention has, compared with a process simply producing acrolein by dehydration of glycerol, the great advantage of consuming less glycerol for the same acrolein production, and of generating less waste since a part of said waste is consumed in order to produce more acrolein. Indeed, during the dehydration step, the main customary "impurity" of the dehydration process is acetaldehyde, often present at 2 to 10 mol %, quite often associated with formaldehyde production in substantial proportions of about 0.1 to 2. In addition, it can be observed that the acrolein produced by aldol condensation is usually subjected to a line of purifications in order to reach the specifications corresponding to its subsequent use. The process of the invention makes it possible to dispense with this phase by virtue of the fact that all of the effluent resulting from the aldol condensation reactor is recycled to step 2.

In another embodiment of the process of the invention, a bio-based formaldehyde obtained from biomethanol will be used as reactant of the third step. This conversion can be obtained according to two slightly different reaction modes. The first consists of an oxidation according to the following reaction:

$$2CH_3OH + O_2 \rightarrow 2HCHO + 2H_2O$$

This reaction is carried out in the gas phase at a temperature between 200° C. and 500° C. at a pressure between 1 and 5 bar absolute, generally a substantially atmospheric pressure, and in the presence of a solid catalyst chosen from iron molybdate, iron tungstate, and mixed oxides of molybdenum and of at least one metal W, V, Cu, Nb, Ti, etc.

In the other reaction mode, the formaldehyde is obtained by oxydehydrogenation of methanol according to the following reaction:

$$CH_3OH \rightarrow HCHO + H_2$$

This reaction is carried out in the gas phase at a temperature between 500° C. and 700° C. in the presence of a silver-metal or copper-metal catalyst at a substantially atmospheric pressure.

It is possible to synthesize the formaldehyde according to a process combining the two reaction modes according to the combination of the following reactions:

$$CH_3OH \rightarrow HCHO + H_2$$

$$2CH_3OH + O_2 \rightarrow 2HCHO + 2H_2O$$

$$2H_2 + O_2 \rightarrow 2H_2O$$

This combination of reactions is carried out in the gas phase at a temperature between 400° C. and 700° C. at a pressure between 1 and 5 bar absolute and in the presence of a solid catalyst chosen from copper metal, silver metal, and silver metal supported on various supports, including silicon carbide, silica, alumina and titanium oxide.

These various reactions are described in Ullmann's Encyclopedia, volume A11, pages 624 to 631, and also in the handbook by the Institut Français du Pétrole [French Institute for Petroleum] "Procédés de pérochimie" ["Petrochemical processes"], volume 1, pages 105 to 114.

When fresh bio-based acetaldehyde must be introduced into the aldol condensation reactor, said acetaldehyde may be synthesized via analogous reactions using bioethanol as described in Ullmann's Encyclopedia, volume A1, pages 34-35, and in the handbook of the Institut Français du Pétrole [French Institute for Petroleum] "Procédés de pétrochimie" ["Petrochemical processes"], volume 2, 1986 edition, pages 33 to 36.

The formaldehyde can be used in the form of an aqueous solution or in anhydrous form, for example paraformaldehyde or trioxane. In the latter cases, the solid formaldehyde derivative is vaporized under a gas stream by heating.

The acrolein obtained according to this process has a $^{14}C/^{12}C$ ratio of generally between 0.9 and $1.2 \times 10^{-12}$ depending on whether or not a fresh non-bio-based formaldehyde and/or acetaldehyde is used. The acrolein obtained will preferably have a ratio of between 1.1 and $1.2 \times 10^{-12}$.

BRIEF DESCRIPTION OF THE DRAWINGS

The process of the invention will be understood more clearly in the light of the description hereinafter, given with reference to the appended figures.

Figure 1:
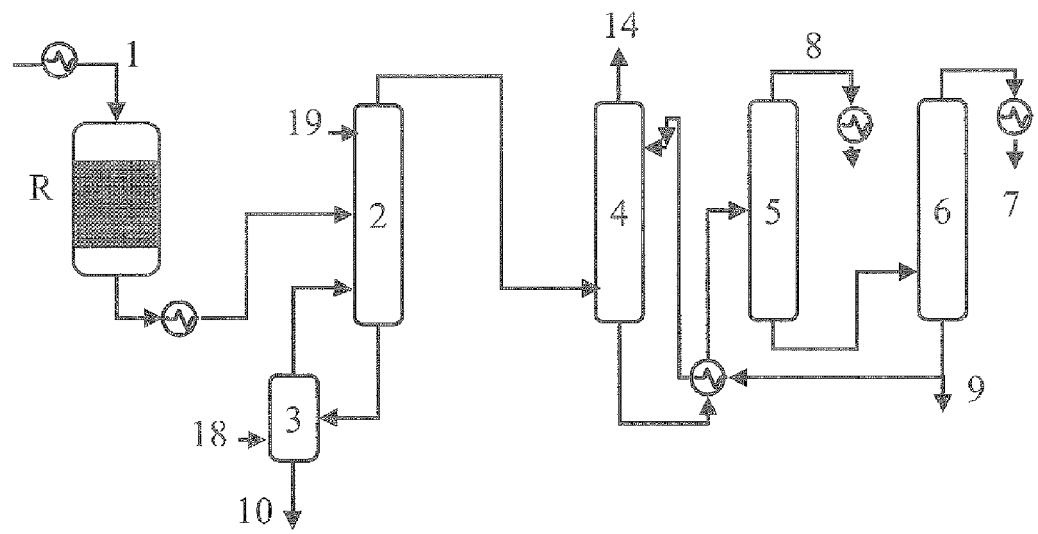
FIG. 1 illustrates steps 1 (dehydration of glycerol) and 2 (condensation and separation of the products) of the process aimed at synthesizing the acrolein, followed by the steps of purification by removal of the heavy compounds and of the noncondensable compounds.

According to FIG. 1, the glycerol charge as a mixture with steam, after preheating, and also oxygen and an inert gas, such as nitrogen, are introduced into the reactor R, containing the acid catalyst, via the line 1. It will be possible, during the operation, to replace all or part of the nitrogen with the noncondensable gases extracted from column 4 via the line 14. The reactor is kept at a temperature between 250 and 350° C. and at a pressure of from 1 to 5 bar. On leaving the reactor, the gaseous effluent is cooled upstream of the condensation column 2. In column 2, where washing is carried out with water introduced via the line 19, the heavy fraction is drawn off at the bottom and is sent to a column 3 where it is subjected to stripping, the objective of which is to recover the light aldehydes that have been entrained in the heavy stream containing the acid and heavy compounds. This stripping of the lightest compounds can optionally be facilitated by using a stripping gas, introduced via the line 18, which may be air, diluted air or recycling gases, for instance those obtained at the top of column 4. The air ($O_2$) can also inhibit polymerization reactions in the columns, with the proviso of using a limited amount thereof so that it does not cause inflammable conditions. The light fraction is extracted at the top of column 3 and recycled at the bottom of column 2. The light fraction of column 2 is removed at the top of the column and sent to a column 4 for removing the noncondensable gases by stripping following the absorption of the aldehydes in the aqueous solution. In this column 4, the noncondensable compounds are extracted at the top of the column and the liquid effluent withdrawn at the bottom of the column is sent, after heating by heat exchange, to a column 5. At the top of column 5, a stream rich in acetaldehyde (and light compounds) is extracted via the line 8, and, at the bottom of this column, an acrolein-enriched aqueous stream is drawn off and sent to column 6. At the top of column 6, the acrolein-rich gas stream is extracted via the line 7, and the water-rich bottom effluent is extracted, of which a fraction is flushed off by extraction, and the main part is recycled via the line 9 to column 4.

Figure 2:
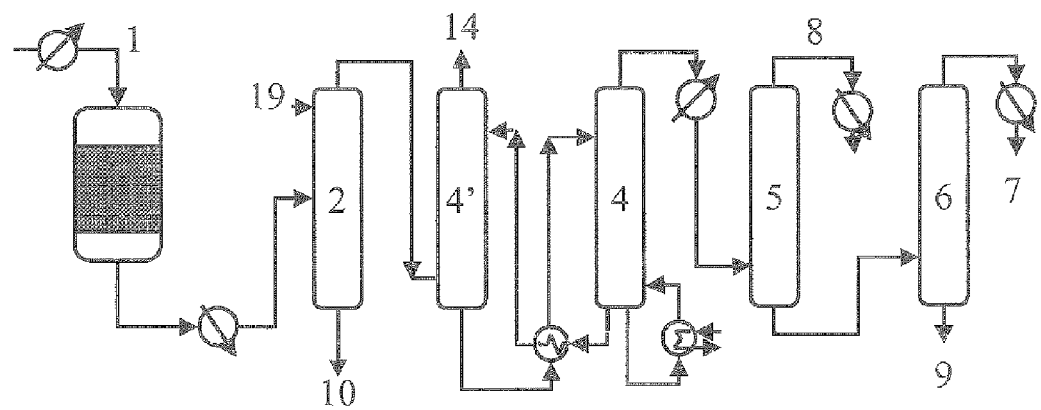
FIG. 2 illustrates a variant of the same process.

The scheme of FIG. 2 illustrates a variant of implementation of the upstream part, steps 1 and 2, of the process, dehydration of glycerol and fractionation of the products. Unlike the scheme of FIG. 1, column 2 is used for the washing with water, introduced according to the arrow 19, of the effluent derived from the reactor, and the heavy compounds are drawn off at the bottom of this column 2 via the line 10. The gas fraction is conveyed to a column 4' from the top of which the noncondensable compounds are extracted via the line 14; this column 4' is coupled with the column 4, the bottom effluent of which is recycled after heating to the top of column 4'. The other components of the scheme are identical to those of FIG. 1, with the sole difference that the recycling of the aqueous solvent of the line 9 is not indicated.

Figure 3:
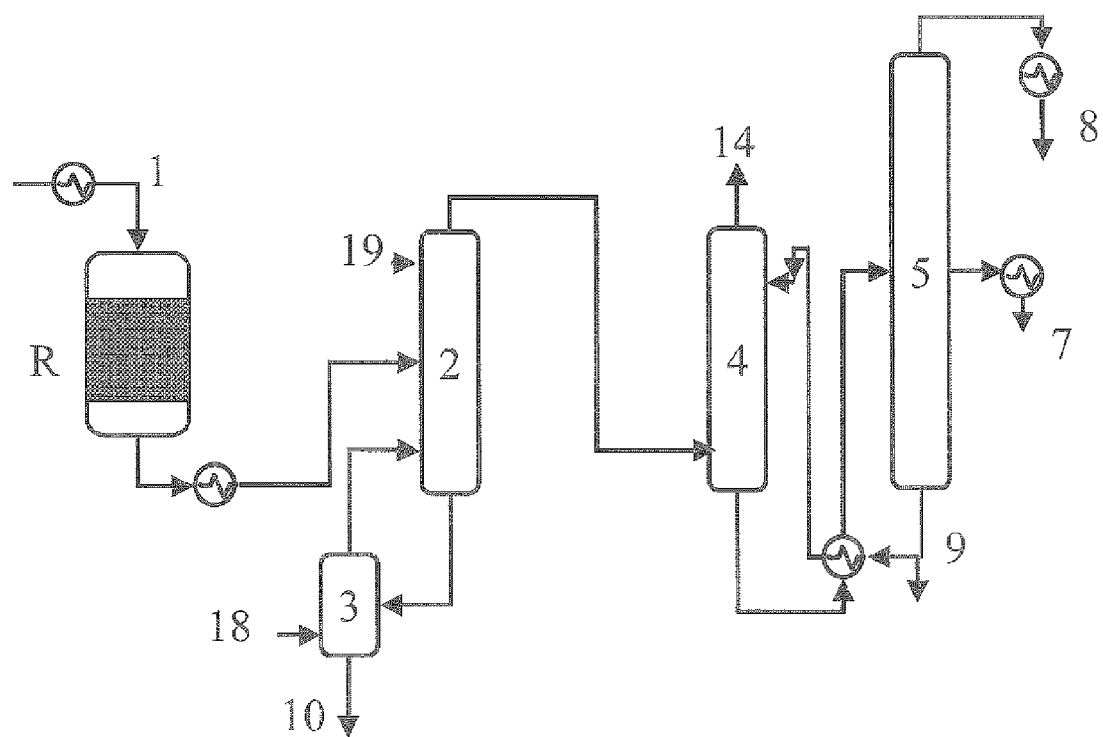
FIG. 3 illustrates steps 1 and 2 of the process with separate extraction of the acetaldehyde and of the acrolein in one and the same column.

The scheme of FIG. 3 is analogous to that of FIG. 1, with the difference that the operating of the column 5 is modified, said column being provided with a side-draw take-off making it possible to simultaneously extract the acrolein-rich gas stream via the line 7, located at an intermediate level, and the acetaldehyde and the light compounds at the top via the line 8. The water-rich bottom effluent of which a fraction is flushed off by extraction and the main part is recycled via the line 9 to column 4.

It should be noted that certain separations by distillation can require elevation of the thermal level; in this case, a reboiler may be inserted at the base of a column requiring this elevation. In order to simplify the presentation, this reboiler and the other auxiliary units are not systematically indicated in the schemes.

Figure 4:
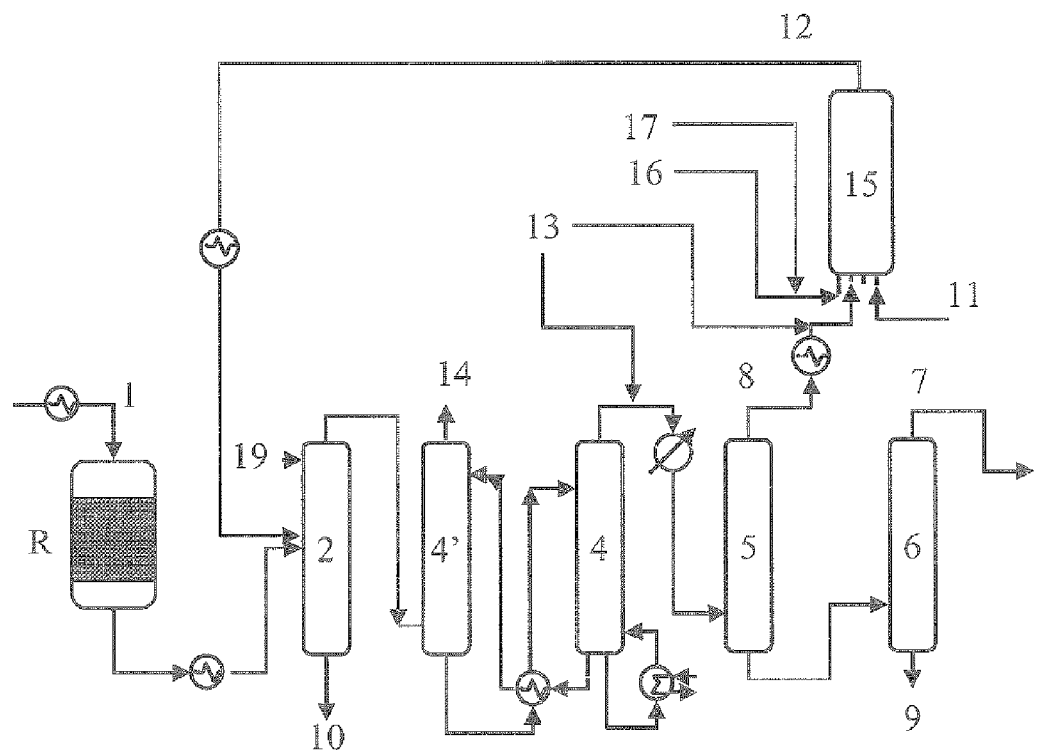
FIG. 4 illustrates the scheme of a complete process with its three steps for synthesizing acrolein, including by aldol condensation of the acetaldehyde and of the formaldehyde resulting from the fractionation phase of step 2 and recycling of the effluent of the aldol condensation reactor at the top of the condensation zone.

FIG. 4 represents the scheme of the whole of a process with its three steps. It is identical to the scheme of FIG. 2 for the entire upstream part of the process, from the reactor R to column 6. Downstream of columns 5 and 6, the stream 8, heated, is sent to the reactor 15 in order to carry out the synthesis of acrolein by aldol condensation of the acetaldehyde contained in the stream 8 and optionally that introduced via the line 13, with the formaldehyde. Additional formaldehyde is optionally introduced via a line 11. Air (or a source of oxygen) is introduced into the reactor 15 via the line 16, and also nitrogen (line 17). This reactor, operating in the gas phase at a temperature of generally between 260 and 350° C., at a pressure generally between 0.8 and 2 bar and a V.V.H. of between 100 and 2500 $h^{-1}$, is provided with the solid condensation reaction catalyst. The gaseous effluent containing the acrolein produced, the unconverted reactants and the other coproducts, including water, is extracted via the line 12 and sent, after cooling, to column 2. The amount of formaldehyde and/or of acetaldehyde required for the reaction, which is not supplied by the line 8, is supplemented with an additional amount via the line 13 or the line 11.

In a preferred variant of implementation of the process for example described with reference to FIG. 4, it will be possible to operate a unit for acrolein production without external supply of acetaldehyde. Indeed, the acrolein-rich effluent resulting from column 6 is removed via the line 7 serving to produce the acrolein as product. Not only does the stream leaving via the line 8 contain acetaldehyde, but, in the case of the conversion of glycerol to acrolein, this acetaldehyde-rich stream also contains formaldehyde. All that is required is for the flow rate of the streams of the line 11 to be selected so that the supplement corresponds to an amount of formaldehyde such that, combined with the contents of constituents and the flow rates for supply of the stream 8 in the reactor 15, the mole ratios selected for the aldol condensation reaction are obtained, this being while optionally dispensing of the supplementary supply via the line 13.

In an analogous manner, should the stream 8 have a formaldehyde content such that the formaldehyde/acetaldehyde mole ratio is greater than that retained for the aldol condensation reaction, the acetaldehyde supplement would be supplied by the line 13.

On the industrial unit, the various components of which it is formed, the size of the reactors in particular, will be defined initially on the basis of "normal" (nominal) operating in terms of capacities. Should the reactor R be operating at a "deficit" relative to its capacity or, for example, in regeneration, a supplementary supply of formaldehyde via 11 and of acetaldehyde via 13 may allow optimal operating of the reactor 15 and, consequently, of the distillation line.

In this configuration of the process scheme, it is not necessary for the separation, in column 5, of the acrolein and the acetaldehyde to be perfect. Column 5 can be regulated in such a way that it allows all the acetaldehyde to pass in the stream 8, and as a result also a certain amount of acrolein at the top with other light aldehydes and ketones. The term "light aldehydes and ketones" is intended to mean those which have boiling points below or equal to acrolein, such as light aldehydes and ketones. Indeed, it is preferable to allow acrolein to pass in the acetaldehyde, and to convey to the separation in column 6 a stream that is less rich in acetalaldehyde, but at the same time has a lower flow rate, without having to excessively enlarge column 5, thereby making it possible to reduce the necessary investments and to more readily adhere to the acrolein quality criteria.

In this configuration via the combination of an acrolein production by dehydration of glycerol and another acrolein production by aldol condensation of acetaldehyde by means of formaldehyde, the streams are exploited better, which, consequently, facilitates industrial application.

Figure 5:
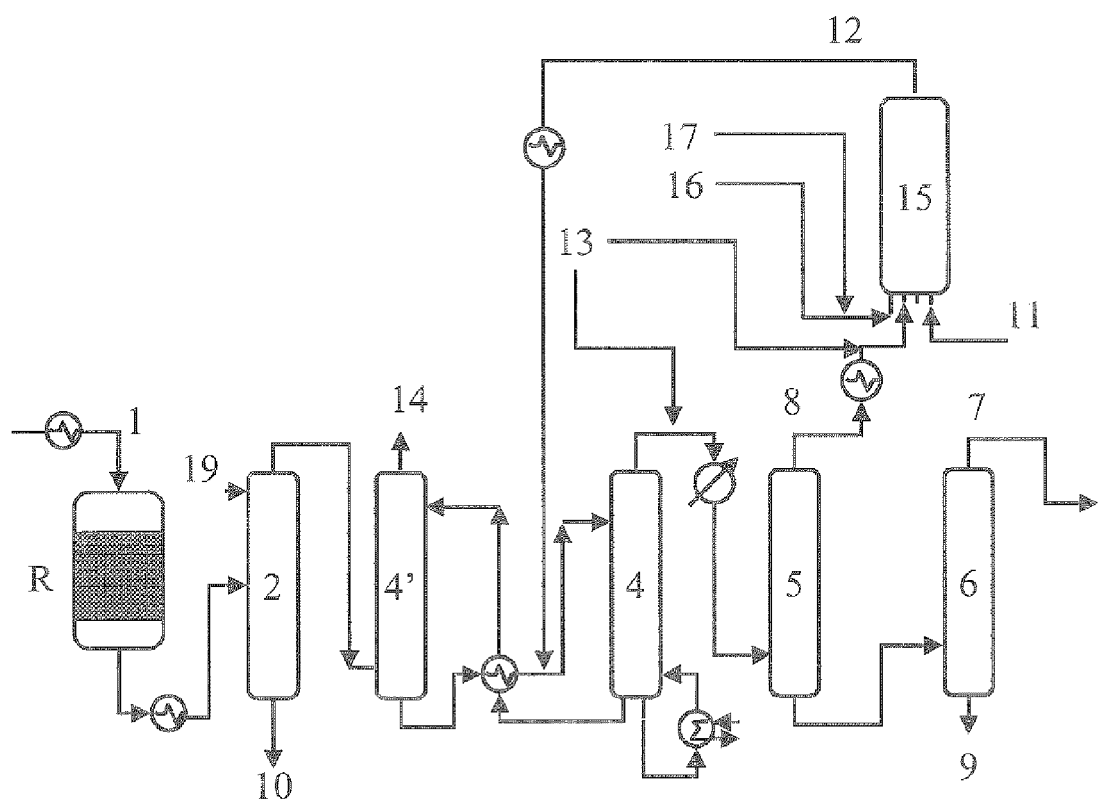
FIG. 5 illustrates a variant of the process according to which the recycling via the line 12 takes place in the condensation zone downstream of the heavy-compound-removing column.

FIG. 5 illustrates a variant of the process according to which the acrolein synthesized by means of a reaction in which there is aldol condensation between acetaldehyde and formaldehyde is sent, via the line 12 after cooling, to the condensation zone downstream of column 4' and/or upstream of column 4. According to this process scheme, the stream 12 is sent back into the stream going from column 4' to column 4, and is used for washing the noncondensable gases. The acetaldehyde and the acrolein will be absorbed and eliminated at the top of column 4, the heavy compounds produced will be returned with water to column 4'. The advantage of this configuration is that the hot stream coming from 12 makes it possible to heat the stream going from column 4' to column 4. In the event of a supplementary supply of acetaldehyde, this may be carried out either at the level of the line 8 or upstream of column 5 where the separation of the light aldehydes and of the acrolein takes place.

Figure 6:
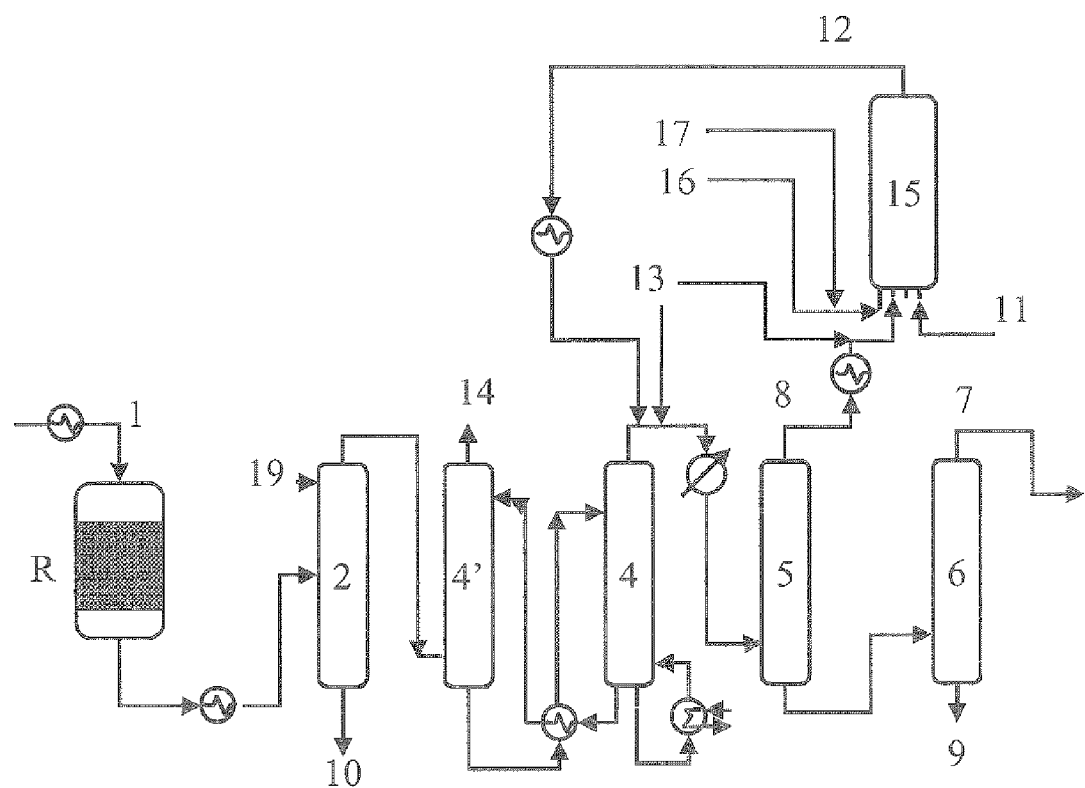
FIG. 6 illustrates a variant of the process according to which the recycling via the line 12 takes place at the input of the fractionation zone.

FIG. 6 illustrates a variant of the process according to which the acrolein synthesized by means of a reaction in which there is aldol condensation between acetaldehyde and formaldehyde is sent, via the line 12 after cooling, to the input of the fractionation zone in the stream going from column 4 to column 5.

According to this configuration of the process, since the stream 12 contains mainly acrolein, acetaldehyde and water, the latter are conveyed to column 5, where the acetaldehyde which has not been converted is distilled again. If the conversion in the reactor 15 is partial, then acetaldehyde accumulates in this loop, till an equilibrium concentration is reached, such that the amount of acetaldehyde produced in the reactor R is approximately equal to that converted in the reactor 15. Any heavy products formed in the reactor 15 are removed in 9.

In these configurations, the propanaldehyde is removed with the acrolein and is not therefore conveyed with the acetaldehyde to the reactor 15. There is therefore no formation of methacrolein in this process, and there is therefore no need to seek to separate it.

Figure 7:
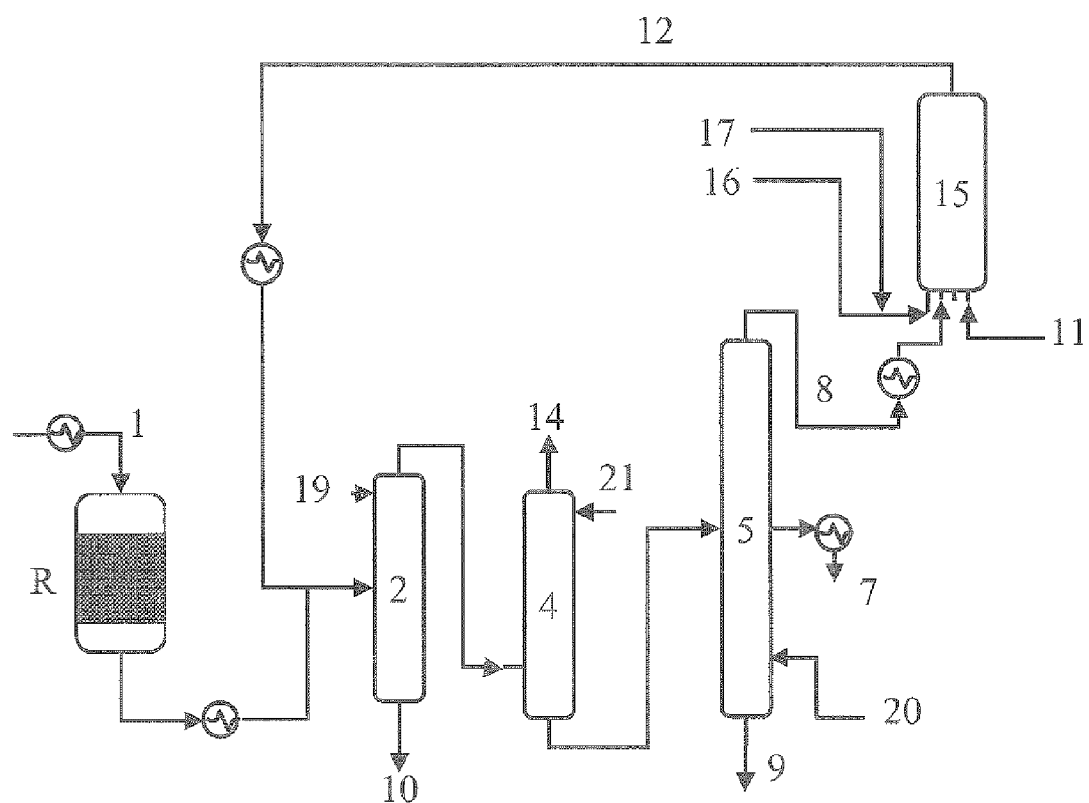
FIG. 7 illustrates a variant of the process implementing the scheme of FIG. 4 with, however, a fractionation zone having a single column as illustrated in FIG. 3.

FIG. 7 illustrates a variant of the process implementing the scheme of FIG. 4 with a simplified fractionation zone comprising a single column analogous to that of FIG. 3. In this variant, without recycling of the aqueous effluent of the line 9, steam at a pressure of 4 bar is injected at the bottom of column 5 via the line 20, and absorption water is injected at the top of column 4 via the line 21.

The process of the invention is illustrated by the following examples.

Example 1 targets the synthesis of acrolein according to the "conventional" process as illustrated by FIG. 2. It is a comparative example.

Example 2 illustrates the process of the invention as illustrated by FIG. 4.

Examples 3 to 6 describe the process implemented according to the scheme described in FIG. 7, while varying the operating conditions of the aldol condensation reactor: amount of formaldehyde, formaldehyde/acetaldehyde ratio, temperature, V.V.H.

Examples 1 (Comparative) and 2

The operating conditions of the reactor R that are implemented in identical fashion in the two examples are the following: Temperature: 320° C.; Pressure: 2.8 bar absolute; Catalyst: tungstated zirconia (ref Z1044 from Dai Ichi Kigenso); VVH of 2250 h$^{-1}$.

The operating conditions of the reactor 15 that are implemented in example 2 are the to following: Temperature: 300° C.; Pressure: 1.3 bar; Catalyst: silica-supported sodium silicate.

The measurements of molar flow rates within the main components of the process are given in tables 1 (comparative example) and 2 (according to the invention) below.

TABLE 1

| Molar flow rate kmol/h | 1 | Output R | Input 4 | Input 5 | Input 6 | 8 | 7 |
|---|---|---|---|---|---|---|---|
| GLYCEROL | 3.274 | 0.033 | 0.000 | 0.000 | 0.000 | 0.000 | 0.000 |
| WATER | 41.112 | 47.661 | 105.059 | 0.319 | 0.319 | 0.000 | 0.105 |
| O$_2$ | 2.972 | 2.467 | 0.074 | 0.005 | 0.000 | 0.005 | 0.000 |
| ARGON | 0.062 | 0.062 | 0.002 | 0.000 | 0.000 | 0.000 | 0.000 |
| ACROLEIN | 0.001 | 2.620 | 2.580 | 2.511 | 2.511 | 0.000 | 2.511 |
| CO$_2$ | 7.139 | 7.336 | 0.954 | 0.210 | 0.000 | 0.210 | 0.000 |
| ACETALDEHYDE | 0.000 | 0.295 | 0.286 | 0.265 | 0.000 | 0.265 | 0.000 |
| ACETONE | 0.000 | 0.003 | 0.003 | 0.003 | 0.003 | 0.000 | 0.003 |
| PROPIONALDEHYDE | 0.000 | 0.016 | 0.005 | 0.005 | 0.005 | 0.000 | 0.005 |
| GLYCERYL ACETAL | 0.000 | 0.008 | 0.000 | 0.000 | 0.000 | 0.000 | 0.000 |
| ACRYLIC ACID | 0.000 | 0.033 | 0.000 | 0.000 | 0.000 | 0.000 | 0.000 |
| CO | 0.003 | 0.393 | 0.012 | 0.000 | 0.000 | 0.000 | 0.000 |
| ACETIC ACID | 0.000 | 0.049 | 0.000 | 0.000 | 0.000 | 0.000 | 0.000 |
| PROPIONIC ACID | 0.000 | 0.003 | 0.000 | 0.000 | 0.000 | 0.000 | 0.000 |
| ALLYL ALCOHOL | 0.000 | 0.007 | 0.000 | 0.000 | 0.000 | 0.000 | 0.000 |
| FORMALDEHYDE | 0.001 | 0.246 | 0.238 | 0.179 | 0.179 | 0.000 | 0.000 |
| FORMIC ACID | 0.000 | 0.010 | 0.000 | 0.000 | 0.000 | 0.000 | 0.000 |
| HYDROXYACETONE | 0.000 | 0.033 | 0.000 | 0.000 | 0.000 | 0.000 | 0.000 |
| Temperature | 320° C. | | 70° C. | 5° C. | | | |
| Pressure | 2.8 bar | | 1.7 bar | 1.7 bar | | | |

TABLE 2

| Molar flow rate kmol/h | 1 | Output R | Input 2 | Input 4 | Input 5 | Input 6 | 8 | 7 | 11 | 12 |
|---|---|---|---|---|---|---|---|---|---|---|
| GLYCEROL | 3.274 | 0.033 | 0.033 | 0.000 | 0.000 | 0.000 | 0.000 | 0.000 | 0.000 | 0.000 |
| WATER | 41.112 | 47.661 | 49.009 | 106.054 | 0.344 | 0.344 | 0.000 | 0.113 | 1.145 | 1.348 |
| O$_2$ | 2.972 | 2.467 | 2.467 | 0.074 | 0.005 | 0.000 | 0.005 | 0.000 | 0.000 | 0.000 |
| ARGON | 0.062 | 0.062 | 0.062 | 0.002 | 0.000 | 0.000 | 0.000 | 0.000 | 0.000 | 0.000 |
| ACROLEIN | 0.001 | 2.620 | 2.823 | 2.780 | 2.705 | 2.705 | 0.000 | 2.705 | 0.000 | 0.203 |
| CO$_2$ | 7.139 | 7.336 | 7.336 | 0.954 | 0.210 | 0.000 | 0.210 | 0.000 | 0.000 | 0.000 |
| ACETALDEHYDE | 0.000 | 0.295 | 0.404 | 0.391 | 0.363 | 0.000 | 0.363 | 0.000 | 0.000 | 0.109 |
| ACETONE | 0.000 | 0.003 | 0.003 | 0.003 | 0.003 | 0.003 | 0.000 | 0.003 | 0.000 | 0.000 |
| PROPIONALDEHYDE | 0.000 | 0.016 | 0.016 | 0.005 | 0.005 | 0.005 | 0.000 | 0.005 | 0.000 | 0.000 |
| GLYCERYL ACETAL | 0.000 | 0.008 | 0.008 | 0.000 | 0.000 | 0.000 | 0.000 | 0.000 | 0.000 | 0.000 |
| ACRYLIC ACID | 0.000 | 0.033 | 0.033 | 0.000 | 0.000 | 0.000 | 0.000 | 0.000 | 0.000 | 0.000 |
| CO | 0.003 | 0.393 | 0.393 | 0.012 | 0.000 | 0.000 | 0.000 | 0.000 | 0.000 | 0.000 |
| ACETIC ACID | 0.000 | 0.049 | 0.049 | 0.000 | 0.000 | 0.000 | 0.000 | 0.000 | 0.000 | 0.000 |
| PROPIONIC ACID | 0.000 | 0.003 | 0.003 | 0.000 | 0.000 | 0.000 | 0.000 | 0.000 | 0.000 | 0.000 |
| ALLYL ALCOHOL | 0.000 | 0.007 | 0.007 | 0.000 | 0.000 | 0.000 | 0.000 | 0.000 | 0.000 | 0.000 |
| FORMALDEHYDE | 0.001 | 0.246 | 0.246 | 0.238 | 0.179 | 0.179 | 0.000 | 0.000 | 0.254 | 0.000 |
| FORMIC ACID | 0.000 | 0.010 | 0.010 | 0.000 | 0.000 | 0.000 | 0.000 | 0.000 | 0.000 | 0.000 |
| HYDROXYACETONE | 0.000 | 0.033 | 0.033 | 0.000 | 0.000 | 0.000 | 0.000 | 0.000 | 0.000 | 0.000 |
| Temperature | 320° C. | | | | 70° C. | 5° C. | | | | |
| Pressure | 2.8 bar | | | | 1.7 bar | 1.7 bar | | | | |

Examples 3 to 6

Examples 3 to 6 are carried out on the basis of the process scheme of FIG. 7. In the interests of simplicity, certain pieces of equipment (compressors, reboilers, condensers, separators, etc.) are intentionally omitted.

The operating conditions of the reactor R for dehydration of glycerol to acrolein are, for these various examples, analogous overall to those of examples 1 and 2. The differences relate to the operating conditions of the aldol condensation reactor 15.

In example 3, an aqueous solution of formaldehyde at 27% by weight and a formaldehyde/acetaldehyde mole ratio of 0.7 are used to supply the reactor 15. The reaction is carried out at a temperature of 300° C. at an HSV of 500 h$^{-1}$ in the presence of the condensation catalyst used in example 2. A detailed analysis of the contents of the various acrolein streams and various compounds is given in table 3; it can be observed that an increase of close to 10% in the acrolein productivity with respect to the acrolein content available at the output of the reactor R is thus obtained.

In example 4, an aqueous solution of formaldehyde at 27% by weight and a formaldehyde/acetaldehyde mole ratio of 0.8 are used to supply the reactor 15. The reaction is carried out at a temperature of 300° C. at an HSV of 300 h$^{-1}$ in the presence of the condensation catalyst used in example 2. A detailed analysis of the contents of the various acrolein streams and various compounds is given in table 4; it can be observed that an increase of close to 10% in the acrolein productivity is thus obtained.

In example 5, paraformaldehyde which is sublimated under a diluted airstream and a formaldehyde/acetaldehyde mole ratio of 0.9 are used to supply the reactor 15. The reaction is carried out at a temperature of 325° C. at an HSV of 750 h$^{-1}$ in the presence of the condensation catalyst used in example 2. A detailed analysis of the contents of the various acrolein streams and various compounds is given in table 5; it can be observed that an increase of close to 10% in the acrolein productivity is thus obtained. In this example, traces of crotonaldehyde are produced and eliminated at the bottom of column 5.

In example 6, a solution of formaldehyde at 50% by weight and a formaldehyde/acetaldehyde mole ratio of 0.8 are used to supply the reactor 15. A small flow rate of air is added to the reactor with the formaldehyde solution. The reaction is carried out at a temperature of 350° C. at an HSV of 300 h$^{-1}$ in the presence of the condensation catalyst used in example 2. A detailed analysis of the contents of the various acrolein streams and various compounds is given in table 6; it can be observed that an increase of close to 10% in the acrolein productivity is thus obtained.

TABLE 3

Example 3

| | Reactor 15 | | | Column 2 | | | |
| --- | --- | --- | --- | --- | --- | --- | --- |
| | | | | Output R | 12 Aldol | | |
| Stream | 8 Acetaldehyde | 11 Formol | 12 Products | Glycerol conv products | condensation products | Top of 2 Top | 10 Residues |
| Temperature (° C.) | 31.2 | 25.0 | 300.1 | 204.4 | 300.1 | 117.9 | 171.3 |
| Pressure (bar) | 3.00 | 3.00 | 3.00 | 1.90 | 3.00 | 1.85 | 1.85 |
| Flow rate by weight kg/h | | | | | | | |
| GLYCEROL | | | | 28.10 | | 0.113 | 27.99 |
| ACROLEIN | 0.003 | | 10.93 | 111.16 | 10.93 | 122.01 | 0.083 |
| WATER | | 19.78 | 24.00 | 690.75 | 24.00 | 711.72 | 3.03 |
| CO | | | 0.239 | 9.27 | 0.239 | 9.51 | |
| CO$_2$ | 0.004 | | 0.004 | 7.27 | 0.004 | 7.27 | 0.001 |
| HYDROXYACETONE | | | | 1.03 | | 1.02 | 0.009 |
| FORMALDEHYDE | | 7.32 | 0.366 | 5.36 | 0.366 | 5.33 | 0.395 |
| ACETALDEHYDE | 15.34 | | 4.60 | 12.75 | 4.60 | 17.34 | 0.006 |
| PROPANALDEHYDE | | | | 0.960 | | 0.959 | |
| ACETONE | | | | 0.160 | | 0.160 | |
| OXYGEN | | | | 20.44 | | 20.44 | |
| NITROGEN | | | | 121.89 | | 121.89 | |

| | Column 4 | | | Column 5 | | | |
| --- | --- | --- | --- | --- | --- | --- | --- |
| Stream | 21 Absorption water | Bottom of 4 Liquid output | 14 Gas output | 20 Vapour 4b | Input 5 Liquid input | 9 Residues | Losses Top | 7 Acrolein prod |
| Temperature (° C.) | 10.0 | 82.8 | 10.0 | 195.0 | 82.8 | 111.5 | 31.1 | 62.7 |
| Pressure (bar) | 2.00 | 1.70 | 1.70 | 5.00 | 1.70 | 1.50 | 1.50 | 1.50 |
| Flow rate by weight kg/h | | | | | | | | |
| GLYCEROL | | 0.113 | | | 0.113 | 0.113 | | |
| ACROLEIN | | 122.01 | 0.003 | | 122.01 | | | 122.01 |
| WATER | 850.00 | 1560.99 | 0.733 | 230.35 | 1560.99 | 1786.2 | | 5.08 |
| CO | | | 9.51 | | | | | |
| CO$_2$ | | 0.005 | 7.27 | | 0.005 | | 0.001 | |
| HYDROXYACETONE | | 1.02 | | | 1.02 | 1.02 | | |
| FORMALDEHYDE | | 5.33 | | | 5.33 | 5.33 | | |
| ACETALDEHYDE | | 17.34 | | | 17.34 | | 0.150 | 1.86 |
| PROPANALDEHYDE | | 0.845 | 0.114 | | 0.845 | | | 0.845 |

TABLE 3-continued

| Example 3 | | | | | | |
|---|---|---|---|---|---|---|
| ACETONE | | 0.160 | | 0.160 | | 0.160 |
| OXYGEN | | | 20.44 | | | |
| NITROGEN | | 0.003 | 121.89 | 0.003 | 0.003 | |

TABLE 4

Example 4

| | Reactor 15 | | | Column 2 | | | |
|---|---|---|---|---|---|---|---|
| | | | | Output R | 12 Aldol | | |
| Flow rate | 8 Acetaldehyde | 11 Formol | 12 Products | Glycerol conv products | condensation products | Top of 2 Top | 10 Residues |
| Temperature (° C.) | 31.2 | 25.0 | 300.1 | 204.4 | 300.1 | 118.0 | 171.5 |
| Pressure (bar) | 3.00 | 3.00 | 3.00 | 1.90 | 3.00 | 1.85 | 1.85 |
| Flow rate by weight kg/h | | | | | | | |
| GLYCEROL | | | | 28.10 | | 0.116 | 27.99 |
| ACROLEIN | 0.002 | | 12.53 | 111.16 | 12.53 | 123.61 | 0.083 |
| WATER | | 22.68 | 27.20 | 690.73 | 27.20 | 714.92 | 3.01 |
| CO | | | 0.152 | 9.27 | 0.152 | 9.42 | |
| $CO_2$ | 0.004 | | 0.004 | 7.27 | 0.004 | 7.27 | 0.001 |
| HYDROXYACETONE | | | | 1.03 | | 1.02 | 0.009 |
| FORMALDEHYDE | | 8.39 | 0.419 | 5.36 | 0.419 | 5.39 | 0.394 |
| ACETALDEHYDE | 15.39 | | 4.62 | 12.75 | 4.62 | 17.36 | 0.006 |
| PROPANALDEHYDE | | | | 0.960 | | 0.959 | |
| ACETONE | | | | 0.160 | | 0.160 | |
| OXYGEN | | | | 20.44 | | 20.44 | |
| NITROGEN | | | | 121.89 | | 121.89 | |

| | Column 4 | | | Column 5 | | | |
|---|---|---|---|---|---|---|---|
| Flow rate | 21 Absorption water | Bottom of 4 Liquid output | 14 Gas output | 20 Vapour 4b | Input 5 Liquid input | 9 Residues | Losses Top | 7 Acrolein prod |
| Temperature (° C.) | 10.0 | 82.7 | 10.0 | 195.0 | 82.7 | 111.5 | 31.1 | 62.7 |
| Pressure (bar) | 2.00 | 1.70 | 1.70 | 5.00 | 1.70 | 1.50 | 1.50 | 1.50 |
| Flow rate by weight kg/h | | | | | | | | |
| GLYCEROL | | 0.116 | | | 0.116 | 0.116 | | |
| ACROLEIN | | 123.61 | 0.003 | | 123.61 | | | 123.61 |
| WATER | 850.00 | 1564.19 | 0.732 | 237.67 | 1564.19 | 1796.68 | | 5.17 |
| CO | | | 9.42 | | | | | |
| $CO_2$ | | 0.005 | 7.27 | | 0.005 | | 0.001 | |
| HYDROXYACETONE | | 1.02 | | | 1.02 | 1.02 | | |
| FORMALDEHYDE | | 5.39 | | | 5.39 | 5.39 | | |
| ACETALDEHYDE | | 17.36 | | | 17.36 | | 0.151 | 1.82 |
| PROPANALDEHYDE | | 0.846 | 0.113 | | 0.846 | | | 0.846 |
| ACETONE | | 0.160 | | | 0.160 | | | 0.160 |
| OXYGEN | | | 20.44 | | | | | |
| NITROGEN | | 0.003 | 121.89 | | 0.003 | | 0.003 | |

TABLE 5

Example 5

| | Reactor 15 | | | Column 2 | | | |
|---|---|---|---|---|---|---|---|
| | | | | Output R | 12 Aldol | | |
| Stream (line) | 8 Acetaldehyde | 11 Formol | 12 Products | Glycerol conv. products | condensation products | Top of 2 Top | 10 Residues |
| Temperature (° C.) | 30.4 | 25.0 | 350.1 | 204.4 | 350.1 | 117.9 | 172.3 |
| Pressure (bar) | 3.00 | 3.00 | 3.00 | 1.90 | 3.00 | 1.85 | 1.85 |

TABLE 5-continued

Example 5

Flow rate by weight kg/h

| | | | | | | | |
|---|---|---|---|---|---|---|---|
| GLYCEROL | | | | 28.10 | | 0.126 | 27.97 |
| ACROLEIN | 0.002 | | 10.90 | 111.16 | 10.90 | 121.97 | 0.082 |
| WATER | | 0.367 | 4.64 | 690.61 | 4.64 | 692.36 | 2.89 |
| CO | | | 0.209 | 9.27 | 0.209 | 9.47 | |
| $CO_2$ | 0.004 | | 0.214 | 7.28 | 0.214 | 7.49 | 0.001 |
| HYDROXYACETONE | | | | 1.03 | | 1.02 | 0.009 |
| FORMALDEHYDE | | 6.98 | 0.349 | 5.34 | 0.349 | 5.32 | 0.371 |
| ACETALDEHYDE | 11.38 | | 0.569 | 12.75 | 0.569 | 13.31 | 0.004 |
| PROPANALDEHYDE | | | | 0.959 | | 0.959 | |
| CROTONALDEHYDE | | | 1.36 | | 1.36 | 1.35 | 0.003 |
| ACETONE | | | | 0.160 | | 0.160 | |
| OXYGEN | | 0.558 | 0.279 | 20.44 | 0.279 | 20.71 | |
| NITROGEN | | 20.01 | 20.01 | 121.89 | 20.01 | 141.90 | |

| | Column 4 | | | Column 5 | | | |
|---|---|---|---|---|---|---|---|
| Stream (line) | 21 Absorption water | Bottom of 4 Liquid output | 14 Gas output | 20 Vapour 4b | Input 5 Liquid input | 9 Residues | Losses Top | 7 Acrolein prod |
| Temperature (° C.) | 10.0 | 83.3 | 10.0 | 195.0 | 83.3 | 111.5 | 30.3 | 62.7 |
| Pressure (bar) | 2.00 | 1.70 | 1.70 | 5.00 | 1.70 | 1.50 | 1.50 | 1.50 |

Flow rate by weight kg/h

| | | | | | | | | |
|---|---|---|---|---|---|---|---|---|
| GLYCEROL | | 0.126 | | | 0.126 | 0.126 | | |
| ACROLEIN | | 121.97 | 0.006 | | 121.97 | | | 121.97 |
| WATER | 900.00 | 1591.53 | 0.830 | 193.11 | 1591.53 | 1779.54 | | 5.10 |
| CO | | | 9.47 | | | | | |
| $CO_2$ | | 0.006 | 7.48 | | 0.006 | | 0.001 | |
| HYDROXYACETONE | | 1.02 | | | 1.02 | 1.02 | | |
| FORMALDEHYDE | | 5.32 | | | 5.32 | 5.32 | | |
| ACETALDEHYDE | | 13.31 | | | 13.31 | | 0.110 | 1.82 |
| PROPANALDEHYDE | | 0.799 | 0.160 | | 0.799 | | | 0.799 |
| CROTONALDEHYDE | | 1.35 | | | 1.35 | 1.35 | | |
| ACETONE | | 0.160 | | | 0.160 | | | 0.160 |
| OXYGEN | | 0.001 | 20.71 | | 0.001 | | | |
| NITROGEN | | 0.004 | 141.90 | | 0.004 | | 0.003 | |

TABLE 6

Example 6

| | Reactor 15 | | | Column 2 | | | |
|---|---|---|---|---|---|---|---|
| | | | | Output R | 12 Aldol | | |
| Stream | 8 Acetaldehyde | 11 Formol | 12 Products | Glycerol conv. products | condensation products | Top of 2 Top | 10 Residues |
| Temperature (° C.) | 30.9 | 25.0 | 350.0 | 204.4 | 350.0 | 117.9 | 171.4 |
| Pressure (bar) | 3.00 | 3.00 | 3.00 | 1.90 | 3.00 | 1.85 | 1.85 |

Flow rate by weight kg/h

| | | | | | | | |
|---|---|---|---|---|---|---|---|
| GLYCEROL | | | | 28.10 | | 0.111 | 27.99 |
| ACROLEIN | 0.001 | | 9.39 | 111.16 | 9.39 | 120.47 | 0.083 |
| WATER | | 7.34 | 11.65 | 690.74 | 11.65 | 699.37 | 3.01 |
| CO | | | 0.306 | 9.27 | 0.306 | 9.57 | |
| $CO_2$ | 0.004 | | 0.238 | 7.28 | 0.238 | 7.52 | 0.001 |
| HYDROXYACETONE | | | | 1.03 | | 1.02 | 0.010 |
| FORMALDEHYDE | | 7.34 | 0.367 | 5.37 | 0.367 | 5.33 | 0.400 |
| ACETALDEHYDE | 13.46 | | 2.69 | 12.75 | 2.69 | 15.43 | 0.005 |
| PROPANALDEHYDE | | | | 0.960 | | 0.959 | |
| CROTONALDEHYDE | | | 2.14 | | 2.14 | 2.14 | 0.005 |
| ACETONE | | | | 0.160 | | 0.160 | |
| OXYGEN | | 0.328 | 0.016 | 20.43 | 0.016 | 20.45 | |
| NITROGEN | | 1.38 | 1.38 | 121.89 | 1.38 | 123.27 | |

TABLE 6-continued

Example 6

| | Column 4 | | | Column 5 | | | | |
|---|---|---|---|---|---|---|---|---|
| Stream | 21 Absorption water | Bottom of 4 Liquid output | 14 Gas output | 20 Vapour 4b | Input 5 Liquid input | 9 Residues | Losses Top | 7 Acrolein prod |
| Temperature (° C.) | 10.0 | 83.3 | 10.0 | 195.0 | 83.3 | 111.5 | 30.8 | 62.7 |
| Pressure (bar) | 2.00 | 1.70 | 1.70 | 5.00 | 1.70 | 1.50 | 1.50 | 1.50 |
| Flow rate by weight kg/h | | | | | | | | |
| GLYCEROL | | 0.111 | | | 0.111 | 0.111 | | |
| ACROLEIN | | 120.47 | 0.002 | | 120.47 | | | 120.46 |
| WATER | 870.00 | 1568.63 | 0.740 | 213.48 | 1568.63 | 1777.09 | | 5.03 |
| CO | | | 9.57 | | | | | |
| $CO_2$ | | 0.006 | 7.51 | | 0.006 | | 0.001 | |
| HYDROXYACETONE | | 1.02 | | | 1.02 | 1.02 | | |
| FORMALDEHYDE | | 5.33 | | | 5.33 | 5.33 | | |
| ACETALDEHYDE | | 15.43 | | | 15.43 | | 0.131 | 1.85 |
| PROPANALDEHYDE | | 0.852 | 0.107 | | 0.852 | | | 0.852 |
| CROTONALDEHYDE | | 2.14 | | | 2.14 | 2.14 | | |
| ACETONE | | 0.160 | | | 0.160 | | | 0.160 |
| OXYGEN | | 0.001 | 20.45 | | 0.001 | | | |
| NITROGEN | | 0.004 | 123.26 | | 0.004 | | 0.003 | |

The invention claimed is:

1. A process for synthesizing acrolein comprising in a first step, dehydrating a glycerol charge resulting from the methanolysis of plant oils or of animal fats resulting in acrolein according to the reaction $CH_2OH—CHOH—CH_2OH \rightarrow CH_2=CH—CHO+2H_2O$, then, in a second step, after having subjected the effluent resulting from the first step to cooling, in carrying out in a first zone, washing with water and condensation of gaseous effluent resulting from the first step, separating, in a second fractionation zone, firstly a light aldehydes-rich stream, secondly a water-rich stream and thirdly an acrolein stream, and then, in a third step, reacting acetaldehyde contained in the light aldehydes-rich stream preceding with formaldehyde so as to obtain an acrolein-rich second stream by aldol condensation reaction according to the following reaction: $CH_3—CHO+CH_2O \rightarrow CH_2=CHO+H_2O$, and recycling this acrolein-rich second stream to the preceding step 2.

2. The process as claimed in claim 1, wherein the aldol condensation reactor is supplied by the stream of light aldehydes resulting from step 2, which is supplemented with an auxiliary stream of acetaldehyde and/or of formaldehyde such that the acetaldehyde/formaldehyde mole ratio in the reactor is between 0.3 and 1.5.

3. The process as claimed in claim 1, wherein the first glycerol dehydration step is carried out in gas phase in the presence of a solid catalyst at a temperature ranging from 150° C. to 500° C., and a pressure of between 1 and 5 bar.

4. The process as claimed in claim 3, wherein the first glycerol dehydration is carried out in the presence of oxygen.

5. The process as claimed in claim 3, wherein the solid catalyst is made up of homogeneous or multiphase materials, which are insoluble in the reaction medium and which have a Hammett acidity, denoted $H_0$, of less than +2.

6. The process as claimed in claim 1, wherein the aldol condensation reaction of the third step is carried out in the gas phase at a temperature of between 150° C. and 400° C., at a pressure of between 0.5 and 10 bar, in the presence of a solid condensation catalyst.

7. The process as claimed in claim 6, wherein the third step is carried out in the presence of oxygen.

8. The process as claimed in claim 6, wherein the catalyst is a solid such that, firstly, the average $CO_2$, $SO_2$ and $NH_3$ adsorption heats will be, respectively, between 40 and 170 kJ/mol at 303° K. ($CO_2$), between 25 and 180 kJ/mol at 353° K. ($SO_2$) and between 25 and 170 kJ/mol at 423° K. ($NH_3$) and, secondly, the amount of $NH_3$ adsorbed on the surface of the solid will be between 1.5 and 8 micromol/m$^2$ and that of $CO_2$ between 0.5 and 8 micromol/m$^2$.

9. The process as claimed in claim 1, wherein the acrolein-rich second stream resulting from the aldol condensation reaction is recycled to the input of the condensation zone of step 2.

10. The process as claimed in claim 1, wherein the second acrolein-rich stream is recycled to an intermediate point of the condensation zone of step 2, after removal of noncondensable compounds.

11. The process as claimed in claim 1, wherein the second stream is recycled to the input of the fractionation zone of step 2.

12. The process as claimed in claim 1, wherein the aldol condensation reactor is supplied by the stream of light aldehydes resulting from step 2, which is supplemented with an auxiliary stream of acetaldehyde and/or of formaldehyde such that the acetaldehyde/formaldehyde mole ratio in the reactor is between 0.5 and 1.

13. The process as claimed in claim 1, wherein the first glycerol dehydration step is carried out in gas phase in the presence of a solid catalyst at a temperature ranging from 250° C. to 350° C., and a pressure of between 1 and 5 bar.

14. The process as claimed in claim 1, wherein the aldol condensation reaction of the third step is carried out in the gas phase at a temperature of between 260° C. and 350° C., at a pressure of between 0.8 and 2 bar, in the presence of a solid condensation catalyst.

* * * * *